(12) United States Patent
Cho et al.

(10) Patent No.: US 8,124,790 B2
(45) Date of Patent: Feb. 28, 2012

(54) PREPARATION PROCESS USEFUL IN SYNTHESIS OF ATORVASTATIN

(75) Inventors: Dong-Ock Cho, Suwon-si (KR); Younja Kwon, Hwaseong-si (KR); Kyeong-Hoi Cha, Hwaseong-si (KR); Yeongsook Kim, Hwaseong-si (KR); Hyun-Seop Tae, Hwaseong-si (KR)

(73) Assignee: Medichem Korea Co., Ltd., Gyeonggi-do (KR)

( * ) Notice: Subject to any disclaimer, the term of this patent is extended or adjusted under 35 U.S.C. 154(b) by 0 days.

(21) Appl. No.: 12/734,500

(22) PCT Filed: Apr. 4, 2008

(86) PCT No.: PCT/KR2008/001902
§ 371 (c)(1),
(2), (4) Date: Jan. 21, 2011

(87) PCT Pub. No.: WO2009/084773
PCT Pub. Date: Jul. 9, 2009

(65) Prior Publication Data
US 2011/0112309 A1    May 12, 2011

(30) Foreign Application Priority Data
Jan. 2, 2008   (KR) ................ 10-2008-0000083

(51) Int. Cl.
*C07D 207/333*   (2006.01)
*C07D 405/06*    (2006.01)
*C07D 319/06*    (2006.01)

(52) U.S. Cl. ......... 548/517; 548/561; 549/373; 514/423

(58) Field of Classification Search ........................ None
See application file for complete search history.

(56) References Cited

U.S. PATENT DOCUMENTS

| | | |
|---|---|---|
| 5,124,482 A | 6/1992 | Butler et al. |
| 5,216,174 A | 6/1993 | Butler et al. |
| 5,273,995 A | 12/1993 | Roth |
| 2004/0072893 A1 | 4/2004 | Srinath et al. |

FOREIGN PATENT DOCUMENTS

| | | | |
|---|---|---|---|
| EP | 0330172 | | 8/1989 |
| KR | 20080000083 | * | 1/2008 |
| WO | WO9804543 | | 2/1998 |

OTHER PUBLICATIONS

Inhibitors of Cholesterol Biosynthesis 3. Tetrahydro-4-hydroxy-6-[2-(1H-pyrrol-1-yl)ethyl]-2H-pyran-2-one Inhibitors of HMG-CoA Reductase. 2. Effects of Introducing Substituents at Positions three and four of the Pyrrole Nucleus., J. Med. Checm, 1991, 34, pp. 357-366.

* cited by examiner

*Primary Examiner* — Yong Chu
*Assistant Examiner* — Michael Barker
(74) *Attorney, Agent, or Firm* — Cooper & Dunham LLP

(57) ABSTRACT

The present invention relates to a preparation process useful in synthesis of atorvastatin, more particularly a process for preparing atorvastatin is effective in treating hyperlipemia, comprising protecting the dihydroxy group at C3 and C5 positions of the starting material cis-t-butyl-6-substituted-3,5-dihydroxy-hexanoate with trialkyl orthoformate, reducing the terminal nitro or cyano group to amine group, performing N-alkylation by sequentially reacting with ethyl 4-fluorobenzene-2-haloacetate and isobutyryl chloride, cyclizing with N,3-diphenylpropynamide, and performing deprotection and hydrolysis.

11 Claims, No Drawings

PREPARATION PROCESS USEFUL IN SYNTHESIS OF ATORVASTATIN

TECHNICAL FIELD

The present invention relates to a preparation process useful in synthesis of atorvastatin, more particularly a process for preparing atorvastatin of Chemical Formula 1 below, which is effective in treating hyperlipemia, comprising protecting the dihydroxy group at C3 and C5 positions of the starting material cis-t-butyl-6-substituted-3,5-dihydroxy-hexanoate with trialkyl orthoformate, reducing the terminal nitro or cyano group to amine group, performing N-alkylation by sequentially reacting with ethyl 4-fluorobenzene-2-haloacetate and isobutyryl chloride, cyclizing with N,3-diphenylpropynamide, and performing deprotection and hydrolysis:

[Chemical Formula 1]

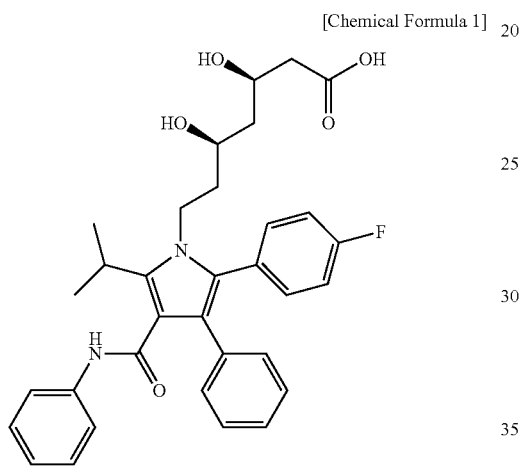

BACKGROUND ART

Atorvastatin is an effective inhibitor of HMG-CoA reductase, and is thus effective in treating hyperlipemia. It has been commercially available in the name of Lipitor™.

There have been numerous researches conducted regarding the synthesis of atorvastatin [WO 98/04543, U.S. Pat. Nos. 5,124,482, 5,216,174 and 5,273,995, U.S. Patent Publication No. 2004/0072893, Korean Patent No. 75791, *J. Med. Chem.*, 1991, 34, 357-366].

The most common process for preparing atorvastatin known so far is shown in Scheme 1 below. According to the preparation process of Scheme 1, the compound of Chemical Formula 10-A with chiral cis-diol structure is obtained by way of the reaction intermediate of the Chemical Formula 16.

[Scheme 1]

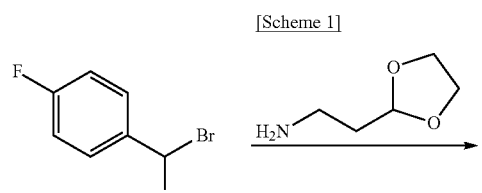

12

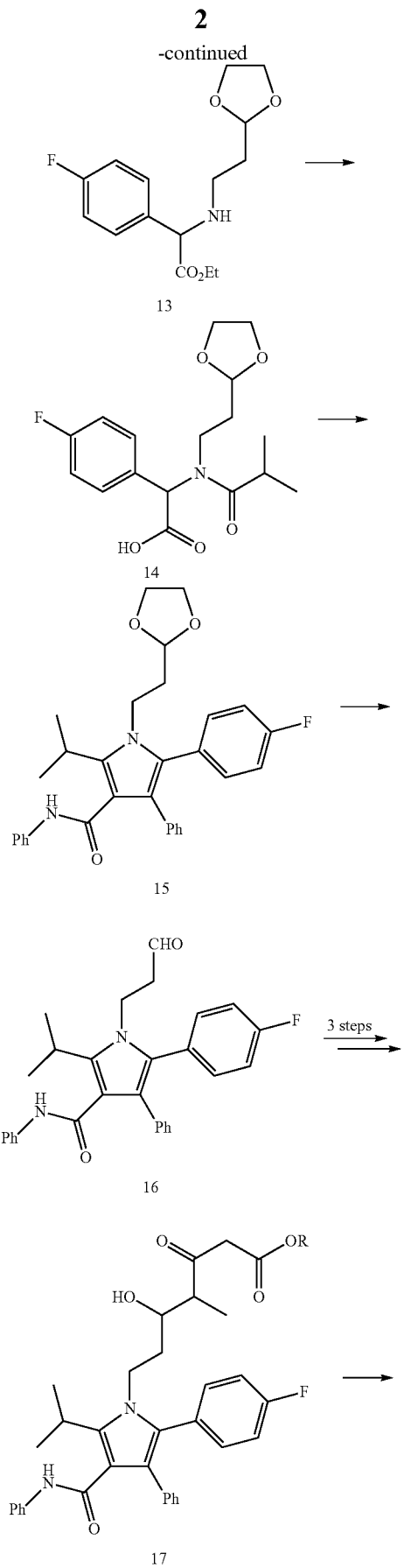

-continued

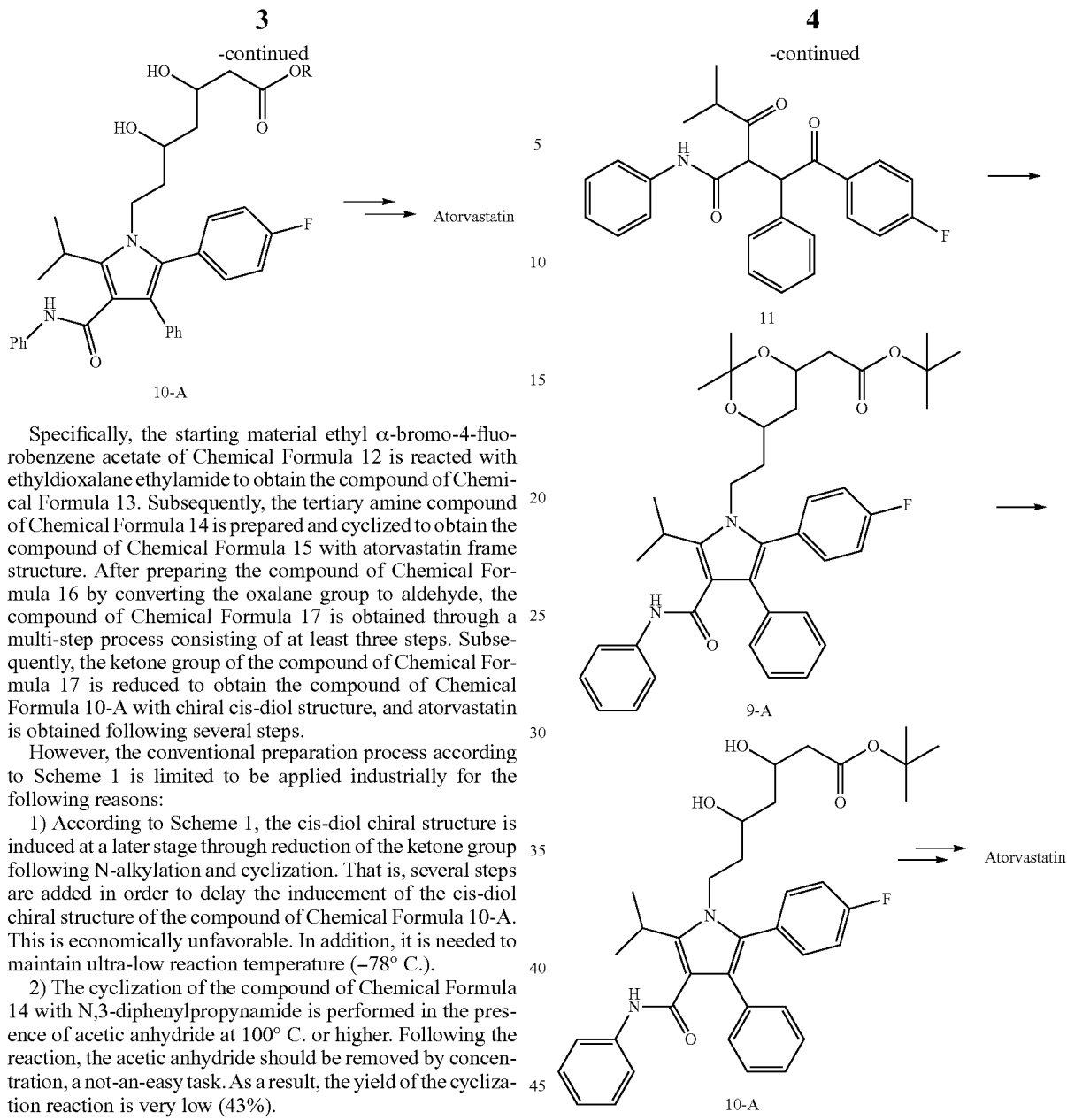

Specifically, the starting material ethyl α-bromo-4-fluorobenzene acetate of Chemical Formula 12 is reacted with ethyldioxalane ethylamide to obtain the compound of Chemical Formula 13. Subsequently, the tertiary amine compound of Chemical Formula 14 is prepared and cyclized to obtain the compound of Chemical Formula 15 with atorvastatin frame structure. After preparing the compound of Chemical Formula 16 by converting the oxalane group to aldehyde, the compound of Chemical Formula 17 is obtained through a multi-step process consisting of at least three steps. Subsequently, the ketone group of the compound of Chemical Formula 17 is reduced to obtain the compound of Chemical Formula 10-A with chiral cis-diol structure, and atorvastatin is obtained following several steps.

However, the conventional preparation process according to Scheme 1 is limited to be applied industrially for the following reasons:

1) According to Scheme 1, the cis-diol chiral structure is induced at a later stage through reduction of the ketone group following N-alkylation and cyclization. That is, several steps are added in order to delay the inducement of the cis-diol chiral structure of the compound of Chemical Formula 10-A. This is economically unfavorable. In addition, it is needed to maintain ultra-low reaction temperature (−78° C.).

2) The cyclization of the compound of Chemical Formula 14 with N,3-diphenylpropynamide is performed in the presence of acetic anhydride at 100° C. or higher. Following the reaction, the acetic anhydride should be removed by concentration, a not-an-easy task. As a result, the yield of the cyclization reaction is very low (43%).

3) The conversion of the oxalane group of the compound of Chemical Formula 15 to aldehyde group has to be performed for a long time of 48 hours under reflux condition, which is limited in industrial application. Also, the yield is not good (68.5%).

For the aforesaid reasons, the process for preparing atorvastatin according to Scheme 1 is not industrially applicable. Therefore, an improved version of the process for preparing atorvastatin was disclosed based on the conventional method according to Scheme 1 and is summarized in Scheme 2 below:

In the preparation process according to Scheme 2, the compound of Chemical Formula 10-A with a frame structure of atorvastatin is prepared following the cyclization of the compound of Chemical Formula 4-A and the compound of Chemical Formula 11.

The compound of Chemical Formula 4-A and the compound of Chemical Formula subjected to the cyclization are prepared by Schemes 2a and 2b, respectively:

[Scheme 2]

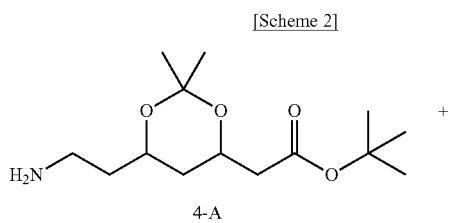

[Scheme 2a]

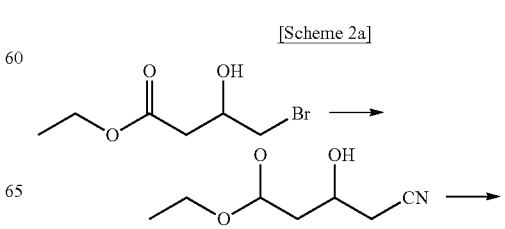

-continued

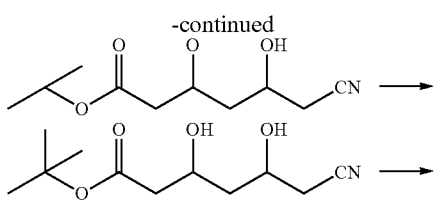

2-A

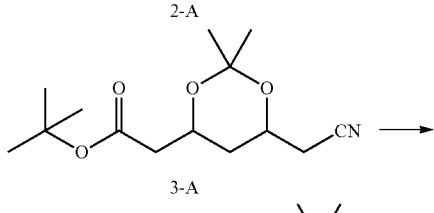

3-A

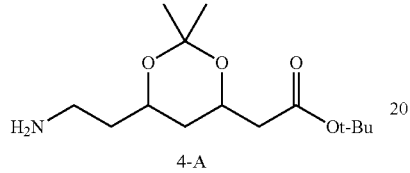

4-A

[Scheme 2b]

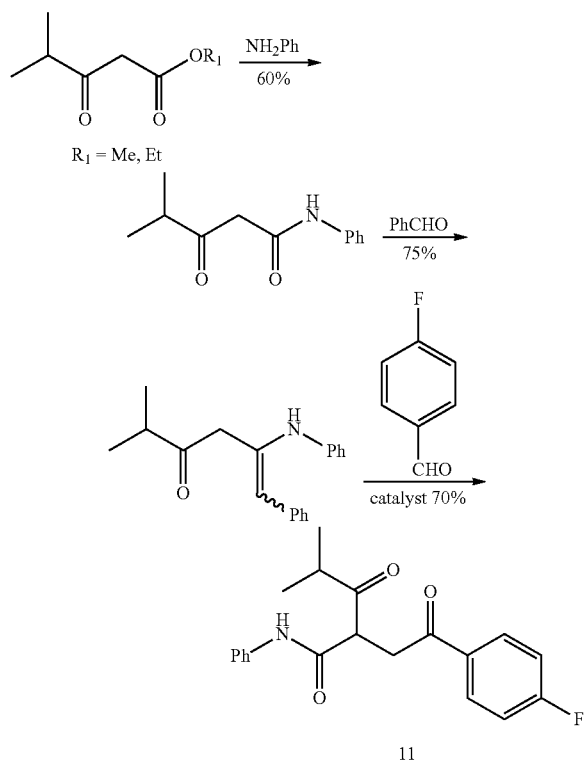

However, the improved preparation process according to Scheme 2 is also limited in its industrial applications for the following reasons:

1) The cyclization to prepare the compound of Chemical Formula 9-A has to be performed at 100° C. or higher for over 48 hours.

2) The compounds used in the cyclization are prepared through multi-step processes. Especially, with the preparation yield of the 4-(4-fluorophenyl)-2-isobutyryl-3-phenyl-4-oxo-N-phenyl-butyrylamide compound of Chemical Formula 11 being 35% or below, the synthesis process of the reactants is uneconomical.

3) Because the chiral dihydroxy group of the compound of Chemical Formula 9-A is protected by 2,2-dimethyldioxane, deprotection is not easy.

4) In order to deprotect the compound of Chemical Formula 9-A, the compound has to be exposed to 80° C. or higher over 8 hours in the presence of excess (20% w/v or more, based on the compound) acid. Further, the yield is only 65% or below.

For the aforesaid reasons, the improved process for preparing atorvastatin according to Scheme 2 is also industrially inapplicable, because it requires a harsh reaction condition and gives low production yield and purity.

As an alternative, Korean Patent Publication No. 2004-84915 has disclosed a compound of Chemical Formula 4-B as intermediate for synthesis of atorvastatin, which has a chemical structure relatively easy to protect and deprotect:

[Chemical Formula 4-B]

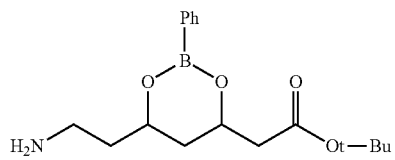

When compared with the compound of Chemical Formula 4-A, in which the dihydroxy group is protected by 2,2-dimethyldioxane, the compound of Chemical Formula 4-B requires a milder condition for protection and deprotection and provides improved yield.

As described above, the conventional preparation processes of atorvastatin of Chemical Formula 1 are limited in industrial application.

DISCLOSURE

Technical Problem

An object of the present invention is to provide a novel process for preparing atorvastatin of Chemical Formula 1, which is industrially applicable and provides the target atorvastatin compound with high yield and purity, without impurities.

Technical Solution

The present invention has been made in an effort to solve the above-described problems associated with the prior art.

In an aspect, the present invention provides a process for preparing atorvastatin according to Scheme 3 below, which comprises the steps of:

i) protecting cis-t-butyl-6-substituted-3,5-dihydroxy-hexanoate of Chemical Formula 2 with trialkyl orthoformate of the formula $CH(OR_2)_3$ to obtain cis-t-butyl-2-alkoxy-3,5-dioxane-6-substituted-hexanoate of Chemical Formula 3;

ii) reducing the terminal nitro or cyano group of the cis-t-butyl-2-alkoxy-3,5-dioxane-6-substituted-hexanoate of Chemical Formula 3 to obtain cis-t-butyl-2-alkoxy-3,5-dioxane-7-amino-heptanoate of Chemical Formula 4;

iii) N-alkylating the cis-t-butyl-2-alkoxy-3,5-dioxane-7-amino-heptanoate of Chemical Formula 4 by sequentially reacting with ethyl 4-fluorobenzene-2-haloacetate and isobutyryl chloride to obtain cis-t-butyl-2-alkoxy-3,5-dioxane-6-N,N-disubstituted amino-heptanoate of Chemical Formula 7;

iv) cyclizing the cis-t-butyl-2-alkoxy-3,5-dioxane-6-N,N-disubstituted amino-heptanoate of Chemical Formula 7 with N,3-diphenylpropynamide to obtain 5-(4-fluorophenyl)-2-(1-methylethyl)-1-(cis-t-butyl-2-alkoxy-3,5-dioxane-7-amido-heptanoate)-N,4-diphenyl-1H-pyrrole-3-carboxamide of Chemical Formula 9;

v) deprotecting the 5-(4-fluorophenyl)-2-(1-methylethyl)-1-(cis-t-butyl-2-alkoxy-3,5-dioxane-7-amido-heptanoate)-N,4-diphenyl-1H-pyrrole-3-carboxamide of Chemical Formula 9 in alcohol solvent in the presence of acid catalyst, and hydrolyzing in aqueous solution to obtain atorvastatin of Chemical Formula 1:

where $R_1$ is nitromethyl ($CH_2NO_2$) or cyano (CN); $R_2$ is H, $C_1$-$C_6$ alkyl, substituted or unsubstituted phenyl, or substituted or unsubstituted naphtyl; $R_2$ and $R_3$ are independently H, $C_1$-$C_6$ alkyl, substituted or unsubstituted phenyl, or substituted or unsubstituted naphtyl; and X is halogen.

The compounds of Chemical Formula 4, Chemical Formula 7 and Chemical Formula 9, which are obtained as reaction intermediates during the preparation process according to Scheme 3, are novel compounds. In another aspect, the present invention provides the novel compounds of Chemical Formula 4, Chemical Formula 7 and Chemical Formula 9.

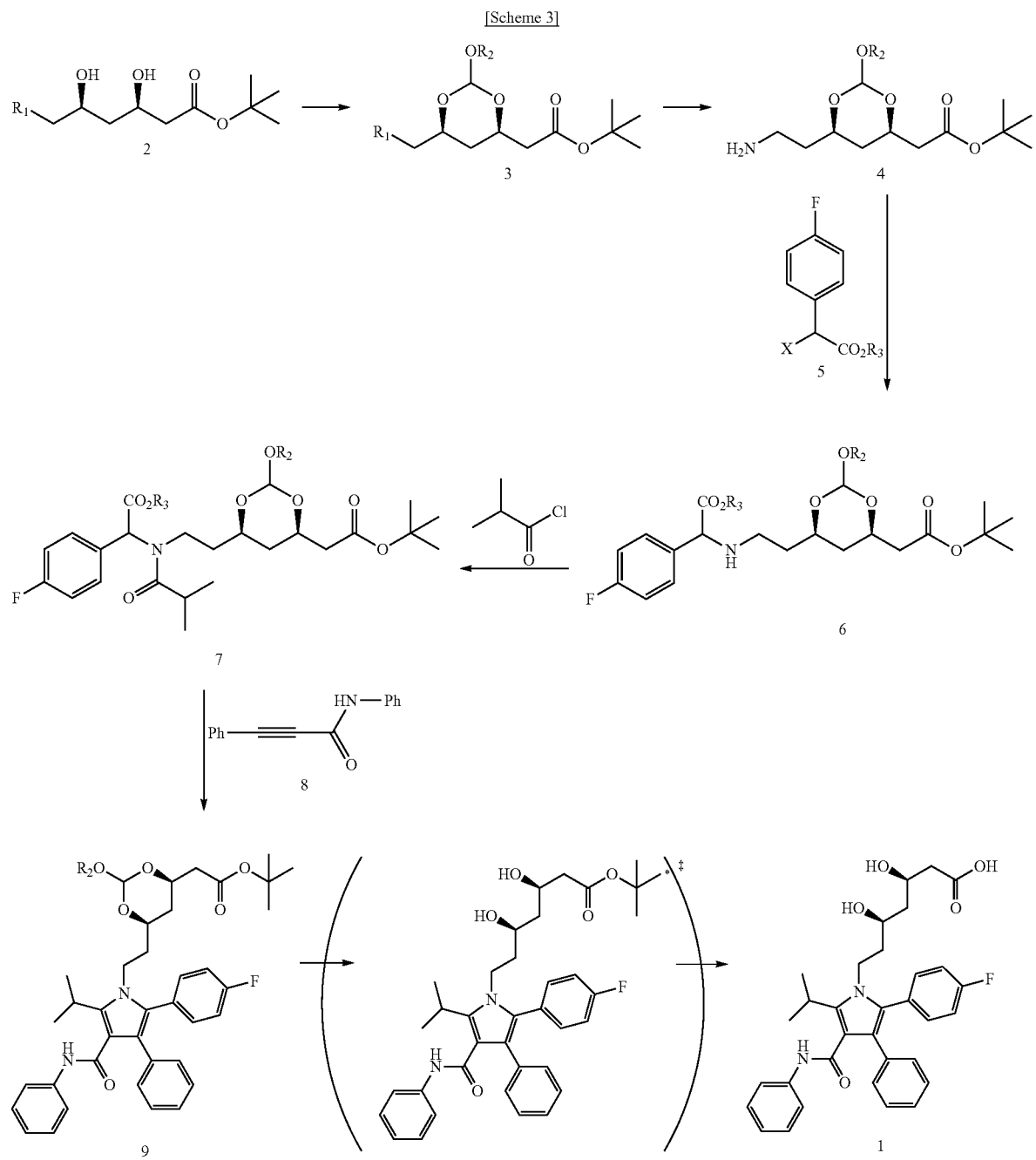

Advantageous Effects

The process for preparing atorvastatin of Chemical Formula 1 according to the present invention provides the following advantageous effects:

1) After synthesizing a chiral diol intermediate with the dihydroxy group protected in an early stage, the functional group of atorvastatin is introduced with high yield, and then cyclization is carried out. As a result, each of the intermediates is produced with high purity of 96% (HPLC area %) or better.

2) Trialkyl orthoformate is selectively used as a protecting agent of the dihydroxy group. As a result, although 4 out of the 7 steps of are performed at room temperature of below, the wanted target compounds can be obtained almost quantitatively within 1-2 hours.

3) The selective used of trialkyl orthoformate as a protecting agent of the dihydroxy group enables protecting at 0° C. to room temperature, and enables continuous performance of deprotection and hydrolysis. As a result, atorvastatin can be obtained with high yield and purity (98% or better, HP LC area %).

BEST MODE

Reference will now be made in detail to the preparation process and each step thereof according to the present invention.

In step i), the dihydroxy group of cis-t-butyl-6-substituted-3,5-dihydroxy-hexanoate of Chemical Formula 2 is protected. The present invention is characterized in that trialkyl orthoformate of the formula $CH(OR_2)_3$ is selectively used as a protecting agent of the dihydroxy group. The process of introducing the protecting group is described in more detail. The dihydroxy group of cis-t-butyl-6-substituted-3,5-dihydroxy-hexanoate of Chemical Formula 2 can be protected quantitatively using trialkyl orthoformate in adequate solvent in the presence of acid catalyst, under a mild temperature condition of 0° C. to room temperature, preferably 0 to 5° C. The acid catalyst used in the protection may be selected from sulfuric acid, hydrochloric acid, acetic acid, methanesulfonic acid, camphorsulfonic acid (CSA), p-toluenesulfonic acid, etc. Adequate solvent may be selected from tetrahydrofuran (THF), dimethylformamide (DMF), dimethyl sulfoxide (DMSO), diethyl ether, benzene, dichloromethane, acetonitrile, etc.

In step ii), the terminal nitro or cyano group of the compound of Chemical Formula 3 with the dihydroxy group protected is reduced to amino group. The reduction is performed by hydrogenation using mixture solvent of THF and $C_1$-$C_4$ alcohol, in the presence of palladium catalyst and ammonia or ammonium formate. More specifically, of the compound of Chemical Formula 3 with the dihydroxy group protected is hydrogenated in mixture solvent of THF and methanol at 20 to 30° C., in the presence of ammonia or ammonium formate and 10%-palladium/carbon catalyst, to obtain cis-t-butyl-2-alkoxy-3,5-dioxane-7-amino-heptanoate of Chemical Formula 4.

In step iii), the terminal amine group of the compound of Chemical Formula 4 is converted to tertiary amine group by N-alkylation. Ethyl 4-fluorobenzene-2-haloacetate and isobutyryl chloride are used in the N-alkylation as alkylating agents. Through sequential reaction with the alkylating agents, cis-t-butyl-2-alkoxy-3,5-dioxane-6-N,N-disubstituted amino-heptanoate of Chemical Formula 7 is obtained. The N-alkylation is performed at 0 to 5° C. Within 1 to 2 hours, the compound of Chemical Formula 7 can be obtained quantitatively, with high purity (95% or better). Adequate solvent may be selected from tetrahydrofuran (THF), dimethylformamide (DMF), dimethyl sulfoxide (DMSO), diethyl ether, benzene, dichloromethane, acetonitrile, etc. If necessary, base may be added. The base may be an inorganic or organic base commonly used in the related art. Primary, secondary or tertiary organic base, e.g., $C_{1-10}$ alkylamine, pyridine, etc., is preferred.

In step iv), the tertiary amine compound of Chemical Formula 7 is cyclized with N,3-diphenylpropynamide. The cyclization is performed in acetic acid anhydride by heating to 60 to 90° C. to obtain 5-(4-fluorophenyl)-2-(1-methylethyl)-1-(cis-t-butyl-2-alkoxy-3,5-dioxane-7-amido-heptanoate)-N,4-diphenyl-1H-pyrrole-3-carboxamide of Chemical Formula 9.

In step v), the cyclized compound of Chemical Formula 9 is deprotected and hydrolyzed to obtain the target compound atorvastatin of Chemical Formula 1. The deprotection is performed using $C_1$-$C_4$ alcohol and acid catalyst, under a relatively mild reaction condition of 0° C. to room temperature (~25 t). The acid catalyst used in the deprotection may be selected from sulfuric acid, hydrochloric acid, acetic acid, methanesulfonic acid, camphorsulfonic acid (CSA), p-toluenesulfonic acid, etc. Specifically, the deprotection is performed in alcohol solvent such as methanol or ethanol, and then stirring is performed in aqueous HCl solution at 0° C. to room temperature (~25° C.) for 1 to 1.5 hours in order to obtain the compound of Chemical Formula 10. Also, a solvent selected from water, methanol, ethanol, propanol, butanol, acetone, tetrahydrofuran (THF), dichloromethane and a combination thereof may be further used as reaction solvent for the deprotection. Following the deprotection, hydrolysis may be performed consecutively. The hydrolysis is performed in aqueous solution. Specifically, the hydrolysis is performed by adding purified water to the solution containing the compound of Chemical Formula 10, solidifying the compound, dissolving in methanol after removing remaining acid, and consecutively adding an aqueous solution containing sodium hydroxide. When the hydrolysis is completed, acid is added to the reaction solution to adjust pH to from 1 to 4, preferably from 2 to 3, to obtain the target compound atorvastatin of Chemical Formula 1. The deprotection and the hydrolysis are performed consecutively. The yield of the two steps is as high as 88.3%.

As described above, the preparation process of the present invention provides high production yield and purity, although the process is relatively simple and the reaction condition is mild. Accordingly, the preparation process is well suited for industrial application for the production of atorvastatin, which is useful in treating hyperlipemia.

Mode for Invention

The following examples illustrate the present invention and are not intended to limit the same.

EXAMPLE 1

Synthesis of cis-t-butyl-2-methoxy-3,5-dioxane-7-nitro-heptanoate (Chemical Formula 3)

5 g (19.0 mmol) of cis-t-butyl-7-nitro-3,5-dihydroxy-heptanoate was dissolved in 45 mL of THF and cooled to 0° C. After adding 2 drops of $CH_3SO_3H$, 2.5 mL (22.8 mmol) of $CH(OCH_3)_3$ was added slowly. After stirring for 30 minutes while maintaining the temperature constant, the reaction mixture was neutralized with triethylamine (TEA), and then concentrated. After adding 20 mL of $H_2O$, the reaction mixture was extracted with 50 mL of dichloromethane, and then washed with brine. After drying with magnesium sulfate followed by concentration under reduced pressure, the target epimer compound was obtained quantitatively as colorless oil.

$^1$H NMR ($CDCl_3$) ?.29 (s, 9H), 1.4~1.6 (m, 4H), 2.23 (dd, 2H), 2.62 (t, 2H), 3.18 (s, 3H), 3.76 (m, 1H), 4.34 (m, 1H), 5.30 (s, 1H).

EXAMPLE 2

Synthesis of cis-t-butyl-2-ethoxy-3,5-dioxane-7-nitro-heptanoate (Chemical Formula 3)

The target compound was obtained quantitatively in the same manner as in Example 1, except for using $CH(OEt)_3$ as a protecting agent.

$^1$H NMR ($CDCl_3$) 1.0 (t, 3H), 1.28 (s, 9H), 1.4-1.6 (m, 4H), 2.23 (dd, 2H), 2.62 (t, 2H), 3.23 (t, 2H), 3.76 (m, 1H), 4.34 (m, 1H), 5.31 (s, 1H).

EXAMPLE 3

Synthesis of cis-t-butyl-2-methoxy-3,5-dioxane-6-cyano-hexanoate (Chemical Formula 3)

The target compound was obtained quantitatively as colorless oil in the same manner as in Example 1, except for using cis-t-butyl-6-cyano-3,5-dihydroxy-hexanoate (19.0 mmol) as a starting material.

$^1$H NMR ($CDCl_3$) 1.29 (s, 9H), 1.4-1.6 (m, 2H), 2.2-2.7 (m, 4H), 3.18 (s, 3H), 3.76 (m, 1H), 4.34 (m, 1H), 5.30 (s, 1H).

EXAMPLE 4

Synthesis of cis-t-butyl-2-ethoxy-3,5-dioxane-6-cyano-hexanoate (Chemical Formula 3)

The target compound was obtained quantitatively as colorless oil in the same manner as in Example 1, except for cis-t-butyl-6-cyano-3,5-dihydroxy-hexanoate (19.0 mmol) as a starting material and using $CH(OEt)_3$ as a protecting agent.

$^1$H NMR ($CDCl_3$) 1.0 (t, 3H), 1.28 (s, 9H), 1.4-1.6 (m, 2H), 2.2-2.7 (m, 4H), 3.26 (t, 2H), 3.76 (m, 1H), 4.34 (m, 1H), 5.37 (s, 1H).

EXAMPLE 5

Synthesis of cis-t-butyl-2-methoxy-3,5-dioxane-7-amino-heptanoate (Chemical Formula 4)

5 g (18.2 mmol) of the cis-t-butyl-2-methoxy-3,5-dioxane-7-nitro-heptanoate obtained in Example 1 was added to a mixture solvent of 50 mL of MeOH and 50 mL of THF saturated with ammonia. Hydrogenation was performed for 6 hours at room temperature in the presence of 10% Pd/C catalyst. 4.43 g (88.6%) of the target compound was obtained as colorless oil.

$^1$H NMR ($CDCl_3$) 1.29 (s, 9H), 1.4-1.6 (m, 2H), 2.4-2.8 (m, 4H), 3.18 (s, 3H), 3.76 (m, 1H), 4.34 (m, 1H), 5.30 (s, 1H).

EXAMPLE 6

Synthesis of cis-t-butyl-2-methoxy-3,5-dioxane-7-amino-heptanoate (Chemical Formula 4)

4.63 g (92.6%) of the target compound was obtained in the same manner as in Example 5, except for adding 5.7 g (90.8 mmol) of ammonium formate instead of ammonia.

$^1$H NMR ($CDCl_3$) 1.0-1.2 (m, 1H), 1.29 (s, 9H), 1.4-1.6 (m, 2H), 2.2-2.7 (m, 4H), 3.18 (s, 3H), 3.76 (m, 1H), 4.34 (m, 1H), 5.30 (s, 1H).

EXAMPLE 7

Synthesis of cis-t-butyl-2-ethoxy-3,5-dioxane-7-amino-heptanoate (Chemical Formula 4)

The target compound was obtained (yield: 89.8 To) in the same manner as in Example 5, except for using cis-t-butyl-2-ethoxy-3,5-dioxane-7-nitro-heptanoate as a starting material.

$^1$H NMR ($CDCl_3$) 1.0 (t, 3H), 1.28 (s, 9H), 1.4-1.6 (m, 2H), 2.2-2.7 (m, 4H), 3.26 (t, 2H), 3.76 (m, 1H), 4.34 (m, 1H), 5.30 (s, 1H).

EXAMPLE 8

Synthesis of cis-t-butyl-2-methoxy-3,5-dioxane-6-amino-(N-ethyl-(4-fluorobenzene)-acetate)-heptanoate (Chemical Formula 6)

5 g (18.2 mmol) of the cis-t-butyl-2-methoxy-3,5-dioxane-7-amino-heptanoate obtained in Example 5 was dissolved in 50 mL of acetonitrile under nitrogen. After adding triethylamine (TEA; 6.34 mL, 45.5 mmol) and cooling to 0° C., 5.7 g (21.2 mmol) of ethyl 2-bromo-4-fluorobenzeneacetate dissolved in 10 mL of acetonitrile was slowly added. After stirring for 30 minutes and further stirring for 2 hours at room temperature, the reaction mixture was concentrated. After adding 30 mL of 1 N—HCl, the reaction mixture was extracted with 80 mL of dichloromethane. After cooling to 0° C., 20 mL of 2 N—NaOH solution was added and stirring was performed for 30 minutes. The separated organic layer was washed consecutively with water and brine, and filtered after drying with magnesium sulfate. The filtrate was concentrated under reduced pressure to obtain 7.69 g (93.0%) of the target compound.

$^1$H NMR ($CDCl_3$) 1.0-1.2 (m, 4H), 1.29 (s, 9H), 1.4-1.6 (m, 2H), 2.2-2.7 (m, 4H), 3.1-3.4 (m, 5H), 3.56 (s, 1H), 3.76 (m, 1H), 4.34 (m, 1H), 5.36 (s, 1H), 6.7-7.3 (m, 4H).

EXAMPLE 9

Synthesis of cis-t-butyl-2-ethoxy-3,5-dioxane-6-amino(N,N-((4-fluorobenzene)isobutyryl)-acetic acid)-heptanoate (Chemical Formula 7)

15 g (32.9 mmol) of the cis-t-butyl-2-methoxy-3,5-dioxane-6-amino-(N-ethyl-(4-fluorobenzene)-acetate)-heptanoate obtained in Example 8 was dissolved in 150 mL of $CH_2Cl_2$ under nitrogen. After adding triethylamine (TEA; 5.5 mL, 39.54 mmol) and cooling to 0° C., 5.15 mL (49.4 mmol) of isobutyryl dissolved in 30 mL of $CH_2Cl_2$ was slowly added. After stirring for 1.5 hours while maintaining the temperature constant, the reaction mixture was washed consecutively with 30 mL of 2 N—HCl and 100 mL of water, and then concentrated under reduced pressure. After dissolving the concentrate in 20 mL of MeOH, 1.5 g of NaOH dissolved in 10 mL of water was added, and stirring was performed at 0° C. for 1 hour. After concentrating under reduced pressure and adjusting pH to 2.0, the reaction solution was extracted with dichloromethane. The extract was washed with water and brine, dried with magnesium sulfate, and then concentrated to obtain 16.6 g (96.3%) of the target compound as solid.

$^1$H NMR (CDCl$_3$) 1.0-1.2 (m, 10H), 1.29 (s, 9H), 1.4-1.6 (m, 2H), 2.2-2.7 (m, 5H), 3.1-3.4 (m, 5H), 3.56 (s, 1H), 3.76 (m, 1H), 4.34 (m, 1H), 5.30 (s, 1H), 6.7-7.3 (m, 4H).

EXAMPLE 10

Synthesis of 5-(4-fluorophenyl)-2-(1-methylethyl)-1-(cis-t-butyl-2-ethoxy-3,5-dioxane-7-amido-heptanoate)-N,4-diphenyl-1H-pyrrole-3-carboxamide (Chemical Formula 9)

8 g (15.2 mmol) of the cis-t-butyl-2-ethoxy-3,5-dioxane-6-amino(N,N-((4-fluorobenzene)isobutyryl)-acetic acid)-heptanoate obtained in Example 9 and 4.1 g (18.2 mmol) of N,3-diphenylpropynamide was added to 100 mL of acetic acid anhydride under nitrogen, and stirring was performed for 5 hours at 75 to 80° C. After cooling to room temperature and adding 300 mL of cold water, the reaction mixture was extracted with ethyl acetate. The extract was washed again with cold water, and then concentrated. The concentrate was recrystallized in ethyl acetate/hexane to obtain 6.8 g (68.7%) of the target compound as white solid.

$^1$H NMR (DMSO-d6) 1.0-1.3 (m, 18H), 1.4~1.5 (m, 2H), 2.2-2.3 (m, 2H), 2.4 (s, 2H) 3.1-3.2 (m, 5H), 3.6~3.9 (m, 3H), 3.9 (m, 1H), (s, 1H), 5.30 (s, 1H), 6.9-7.5 (m, 14H), 9.84 (s, 1H).

EXAMPLE 11

Synthesis of 5-(4-fluorophenyl)-2-(1-methylethyl)-1-(cis-t-butyl-3,5-dihydroxy-7-amido-heptanoate)-N,4-diphenyl-1H-pyrrole-3-carboxamide (Chemical Formula 10)

10 g of the 5-(4-fluorophenyl)-2-(1-methylethyl)-1-(cis-t-butyl-2-ethoxy-3,5-dioxane-7-amido-heptanoate)-N,4-diphenyl-1H-pyrrole-3-carboxamide obtained in Example 10 was added to 60 mL of MeOH. After adding 6 mL of 2 N—HCl and stirring for 1.5 hours at room temperature, the target compound was obtained quantitatively. The compound was subjected to hydrolysis without further purification.

$^1$H NMR (DMSO-d6) 1.3 (m, 17H), 1.58 (m, 2H), 2.1~2.2 (m, 2H), 2.4~2.5 (bs, 3H), 3.2 (m, 1H), 3.3 (s, 1H), 3.3~3.5 (m, 2H), 4.6~4.7 (m, 2H), 6.9-7.5 (m, 14H), 9.8 (s, 1H).

EXAMPLE 12

Synthesis of Sodium Salt of Atorvastatin (Chemical Formula 1)

The MeOH solution containing the 5-(4-fluorophenyl)-2-(1-methylethyl)-1-(cis-t-butyl-3,5-dihydroxy-7-amido-heptanoate)-N,4-diphenyl-1H-pyrrole-3-carboxamide obtained in Example 11 was cooled to 0° C. and pH was carefully adjusted to 12 using 3 N—NaOH aqueous solution. Stirring was performed at room temperature for 2 hours while maintaining the pH constant. After the complete removal of the starting material was confirmed by TLC (tin layer chromatography) and HPLC, stirring was further performed at 0° C. for 2 hours followed by filtration. The filtered white solid was dried at 35 to 40° C. under reduced pressure to obtain 6.4 g (74.4%) of the sodium salt of atorvastatin as white solid.

$^1$H NMR (DMSO-d$_6$) 9.84 (s, 1H), 7.4-7.9 (m, 2H), 6.9-7.0 (m, 12H), 3.93 (br, 1H), 3.74 (br, 2H), 3.0-3.2 (m, 1H), 2.0-1.93 (m, 4H), 1.2-1.36 (m, 9H).

[Industrial Applicability]

As aforementioned, the process for preparing atorvastatin according to the present invention requires no redundant step for introducing particular functional groups. All the reactions of the 7 steps are performed under relatively mild conditions for a short time. Further, atorvastatin is obtained in high yield. Therefore, the preparation process according to the present invention is industrially applicable.

The present invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:
1. A process for preparing atorvastatin comprising:
  i) protecting cis-t-butyl-6-substituted-3,5-dihydroxy-hexanoate of the following Chemical Formula 2 in the presence of acid catalyst with trialkyl orthoformate of the formula CH(OR$_2$)$_3$ to obtain cis-t-butyl-2-alkoxy-3,5-dioxane-6-substituted-hexanoate of the following Chemical Formula 3:

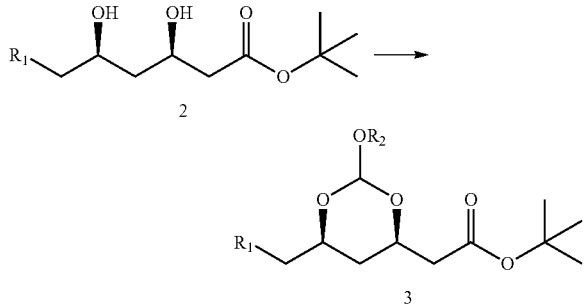

wherein R$_1$ is nitromethyl (CH$_2$NO$_2$) or cyano (CN), and R$_2$ is H, C$_1$-C$_6$ alkyl, substituted or unsubstituted phenyl, or substituted or unsubstituted naphtyl;
  ii) reducing the terminal nitro or cyano group of the cis-t-butyl-2-alkoxy-3,5-dioxane-6-substituted-hexanoate of Chemical Formula 3 to obtain cis-t-butyl-2-alkoxy-3,5-dioxane-7-amino-heptanoate of the following Chemical Formula 4:

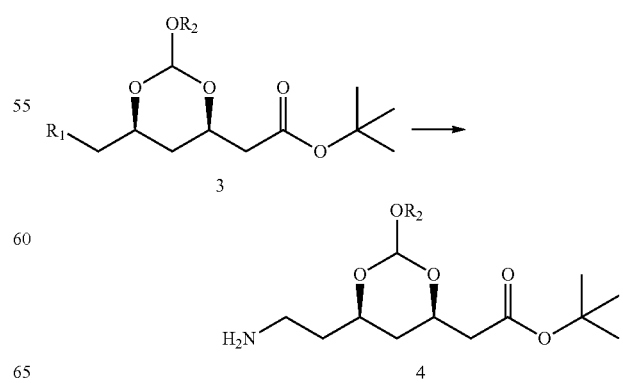

wherein $R_2$ is H, $C_1$-$C_6$ alkyl, substituted or unsubstituted phenyl, or substituted or unsubstituted naphtyl;

iii) N-alkylating the cis-t-butyl-2-alkoxy-3,5-dioxane-7-amino-heptanoate of Chemical Formula 4 by consecutively reacting with ethyl 4-fluorobenzene-2-haloacetate and isobutyryl chloride to obtain cis-t-butyl-2-alkoxy-3,5-dioxane-6-N,N-disubstituted amino-heptanoate of the following Chemical Formula 7:

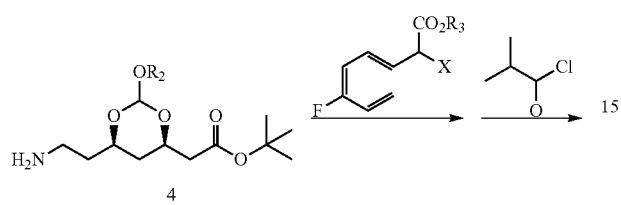

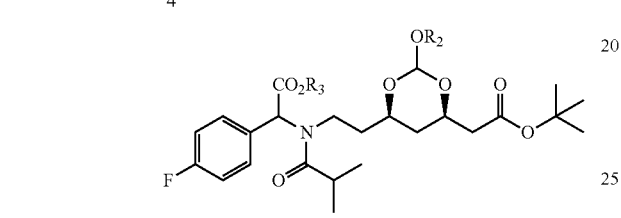

wherein $R_2$ and $R_3$ are independently H, $C_1$-$C_6$ alkyl, substituted or unsubstituted phenyl, or substituted or unsubstituted naphtyl, and X is halogen;

iv) cyclizing the cis-t-butyl-2-alkoxy-3,5-dioxane-6-N,N-disubstituted amino-heptanoate of Chemical Formula 7 with N,3-diphenylpropynamide to obtain 5-(4-fluorophenyl)-2-(1-methylethyl)-1-(cis-t-butyl-2-alkoxy-3,5-dioxane-7-amido-heptanoate)-N,4-diphenyl-1H-pyrrole-3-carboxamide of the following Chemical Formula 9:

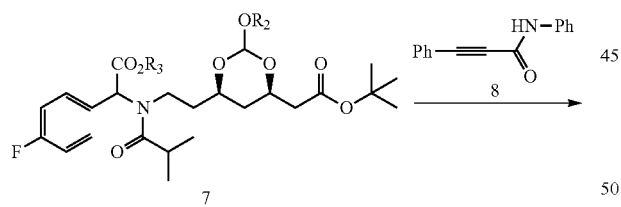

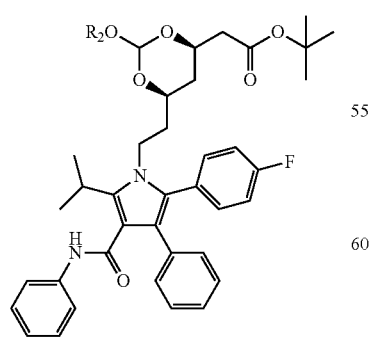

wherein $R_2$ and $R_3$ are independently H, $C_1$-$C_6$ alkyl, substituted or unsubstituted phenyl, or substituted or unsubstituted naphtyl; and v) deprotecting the 5-(4-fluorophenyl)-2-(1-methylethyl)-1-(cis-t-butyl-2-alkoxy-3,5-dioxane-7-amido-heptanoate)-N,4-diphenyl-1H-pyrrole-3-carboxamide of Chemical Formula 9 in alcohol solvent in the presence of acid catalyst, and hydrolyzing in aqueous solution to obtain atorvastatin of the following Chemical Formula 1:

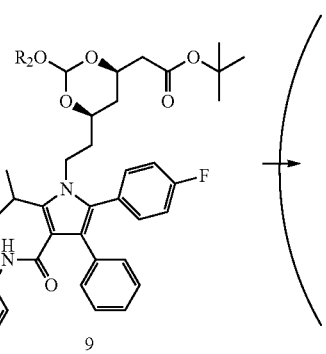

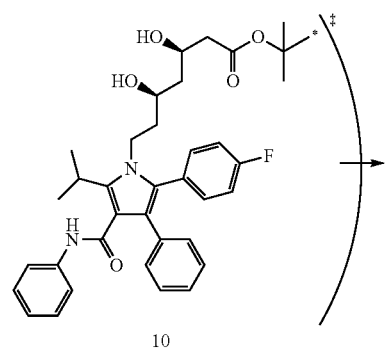

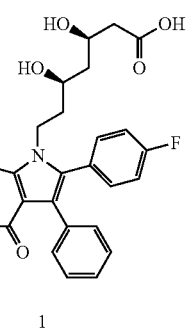

wherein $R_2$ is H, $C_1$-$C_6$ alkyl, substituted or unsubstituted phenyl, or substituted or unsubstituted naphtyl.

2. The process according to claim 1, wherein the protection is performed using an organic solvent selected from tetrahydrofuran (THF), dimethylformamide (DMF), dimethyl sulfoxide (DMSO), diethyl ether, benzene, dichloromethane and acetonitrile.

3. The process according to claim 1, wherein the protection is performed in the presence of an acid catalyst selected from sulfuric acid, hydrochloric acid, acetic acid, methanesulfonic acid, camphorsulfonic acid (CSA) and p-toluenesulfonic acid.

4. The process according to claim 1, wherein the reduction is performed by hydrogenation using a mixture solvent of tetrahydrofuran and alcohol and using palladium catalyst, ammonia or ammonium formate.

5. The process according to claim 1, wherein the N-alkylation is performed in the presence of organic base.

6. The process according to claim 1, wherein the cyclization is performed in acetic acid anhydride by heating at 60 to 90° C.

7. The process according to claim 1, wherein the deprotection is performed using $C_1$-$C_4$ alcohol solvent and using an acid catalyst selected from sulfuric acid, hydrochloric acid, acetic acid, methanesulfonic acid, camphorsulfonic acid (CSA) and p-toluenesulfonic acid at 0 to 25 ° C.

8. The process according to claim 1 or 7, wherein the deprotection is performed further using a solvent selected from water, methanol, ethanol, propanol, butanol, acetone, tetrahydrofuran (THF), dichloromethane and a combination thereof.

9. Cis-t-Butyl-2-alkoxy-3,5-dioxane-7-amino-heptanoate of the following Chemical Formula 4:

[Chemical Formula 4]

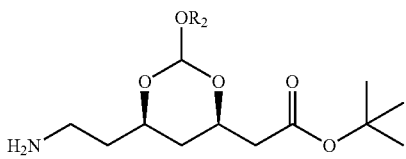

wherein $R_2$ is H, $C_1$-$C_6$ alkyl, substituted or unsubstituted phenyl, or substituted or unsubstituted naphtyl.

10. Cis-t-Butyl-2-alkoxy-3,5-dioxane-6-N,N-disubstituted amino-heptanoate of the following Chemical Formula 7:

[Chemical Formula 7]

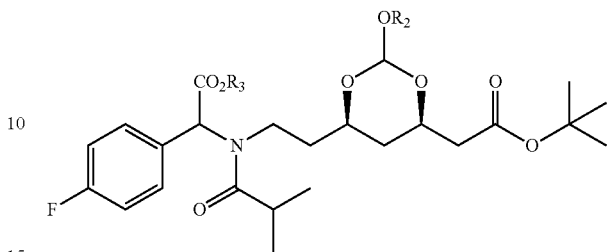

wherein $R_2$ and $R_3$ are independently H, $C_1$-$C_6$ alkyl, substituted or unsubstituted phenyl, or substituted or unsubstituted naphtyl.

11. 5-(4-Fluorophenyl)-2-(1-methylethyl)-1-(cis-t-butyl-2-alkoxy-3,5-dioxane-7-amido-heptanoate)-N,4-diphenyl-1H-pyrrole-3-carboxamide of the following Chemical Formula 9:

[Chemical Formula 9]

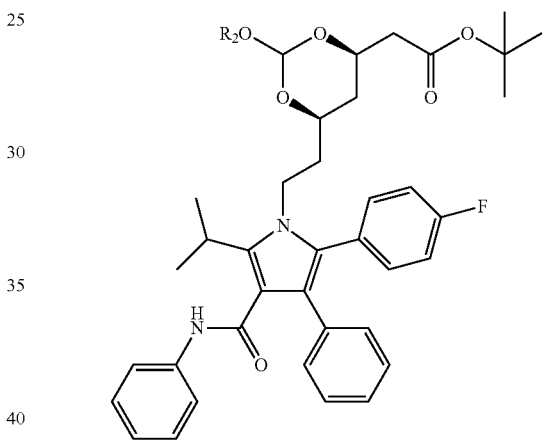

wherein $R_2$ is H, $C_1$-$C_6$ alkyl, substituted or unsubstituted phenyl, or substituted or unsubstituted naphtyl.

* * * * *